United States Patent [19]

Megyeri et al.

[11] Patent Number: 4,816,587

[45] Date of Patent: Mar. 28, 1989

[54] PROCESS FOR THE PREPARATION OF 2-HALOGENATED ERGOLINE DERIVATIVES

[75] Inventors: Gábor Megyeri; Tibor Keve; Lajos Kovács, Jr.; Béla Stefko; Erik Bogsch; Anna Kassia née Zieger; Ferenc Trischler; Gábor Szepesi; Mária Gazdag, all of Budapest, Hungary

[73] Assignee: Richter Gedeon Vegyeszeti Gyar Rt., Budapest, Hungary

[21] Appl. No.: 58,576

[22] Filed: Jun. 5, 1987

[30] Foreign Application Priority Data

Jun. 27, 1986 [HU] Hungary ................ 2690/86

[51] Int. Cl.[4] ............ C07D 457/02; C07D 457/04
[52] U.S. Cl. ........................... 544/346; 546/67; 546/68; 546/69; 260/694
[58] Field of Search ............ 546/67, 68, 69; 544/344, 346; 260/694

[56] References Cited

U.S. PATENT DOCUMENTS

| 3,901,894 | 8/1975 | Kornfeld et al. | 546/67 |
| 3,992,422 | 11/1976 | Green | 540/33 |
| 4,098,790 | 7/1978 | Bach | 546/67 |
| 4,697,017 | 9/1987 | Megyeri et al. | 546/67 |

FOREIGN PATENT DOCUMENTS 904957 6/1986 Belgium .
0208447 1/1987 European Pat. Off. .

OTHER PUBLICATIONS

Phillips, CA 100-175229s, 1984.
Brady et al, CA 105-227273b, 1986.
Milan et al, CA 106-5307x, 1987.
Megyeri et al, CA 106-138686s, 1987.
Bellesia et al, CA 107-96031, 1987.
Troxler et al, Helv. Chem. Acta, 40, 1706 (1957) and 2160 (1957), Substitutionen am Ring System der Lyserpsauce I and III.
Thiem et al, Chem. Ber. 113, 1980, pp. 3075–3085, Synthesen mit Iod–und Bromtrimethylsilan in der Sacharidchemie.
Gillard et al, Tetrahedron Letters, vol. 22, pp. 513–516 (1981), Trimethylsilyl Bromide as a Mild, Stereoselective Anomeric Brominating Agent.
Andreani et al, CA 87-127009m 1977.
Hino et al, CA 88-120918u, 1978.
Rucman et al, CA 89-129780w, 1978.
Da Settimo et al, CA 99-194762n, 1983.

Primary Examiner—Donald G. Daus
Assistant Examiner—Cecilia Shen
Attorney, Agent, or Firm—Herbert Dubno; Jonathan Myers

[57] ABSTRACT

The invention relates to a novel process for the halogenation in 2-position of ergot alkaloids. The process is characterized by that as a halogenating agent a system consisting of dimethylsulfoxide, a trialkylhalosilane or triarylhalosilane and optionally a hydrogen halide is used.

4 Claims, No Drawings

PROCESS FOR THE PREPARATION OF 2-HALOGENATED ERGOLINE DERIVATIVES

The invention relates to a novel process for halogenation in the 2-position of ergot alkaloids and their derivatives.

The invention is based on the recognition that ergot alkaloids containing the structural moiety (IIa)

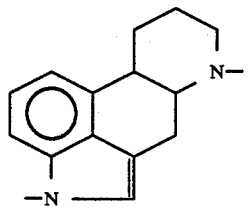

and their derivatives (in the following: ergoline derivatives) can be halogenated in the 2-position with a very high yield and selectivity by using a system consisting of dimethylsulfoxide, a trialkyl- or triarylhalosilane and optionally a hydrogen halide.

Thus, the invention relates to a novel process for the preparation of partially known (partially new) 2-halogenated ergoline derivatives of the formula (I),

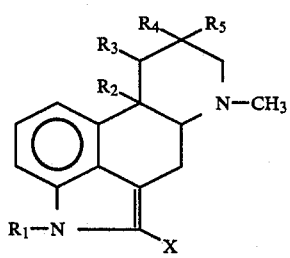

wherein

X stands for a halogen;

$R_1$ stands for hydrogen, a $C_{1-4}$ alkyl group, an acyl group or a substituted acyl group;

$R_2$, $R_3$ and $R_4$ represent hydrogen, or $R_2$ together with $R_3$ or $R_3$ together with $R_4$, respectively, forms an additional chemical bond; and $R_5$ means a hydroxymethyl, methoxycarbonyl or carboxyl group or a —$CH_2$—OR group, wherein R is an acyl or substituted acyl group, or a —$CH_2X$ group, wherein X is a halogen, or a —CO—NH—(a) group,

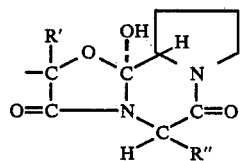

wherein

R' is a methyl or isopropyl group and

R" is a benzyl, isopropyl or isobutyl group; or $R_1$ stands for a methyl group;

$R_2$ is methoxy;

$R_3$ and $R_4$ represent hydrogen and $R_5$ means a hydroxymethyl or a —$CH_2$—OR group, wherein R is a 5-bromonicotinoyl group; or $R_1$ and $R_2$ stand for hydrogen;

$R_3$ and $R_4$ together form an additional chemical bond; and $R_5$ means a methyl group, as well as their acid addition salts.

According to the novel process of the invention, a compound of the formula (II),

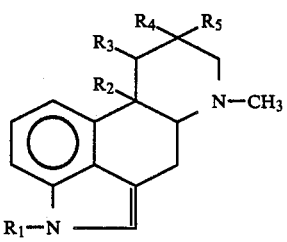

wherein $R_1$, $R_2$, $R_3$, $R_4$ and $R_5$ are as defined above with the proviso that $R_5$ is different from a —$CH_2X$ group, or an acid addition salt thereof, or a crude mixture of ergot alkaloid bases containing several compounds of the formula (II) or a salt of this mixture (a) is halogenated by using a system consisting of dimethylsulfoxide, a trialkylhalosilane or a triarylhalosilane and optionally a hydrogen halide at room temperature and, if desired, the thus-obtained 2-haloergoline derivative of the formula (I), wherein $R_1$, $R_2$, $R_3$ and $R_4$ stand for hydrogen, or $R_2$ together with $R_3$ or $R_3$ together with $R_4$, respectively, forms a chemical bond and $R_5$ means a —$CH_2$—OR group (wherein R is an acyl or substituted acyl group), (i) is N-acylated or N-formylated; or, (ii) if desired, the thus-obtained compound of the formula (I), wherein $R_1$ means a methyl group, $R_2$ stands for methoxy group, both $R_3$ and $R_4$ are hydrogen and $R_5$ is a hydroxymethyl group, are esterified; or, (iii) if desired, the thus-obtained compound of the formula (I), wherein both $R_1$ and $R_4$ are hydrogen, $R_2$ together with $R_3$ forms a chemical bond and $R_5$ is a methoxycarbonyl group, is hydrolyzed; or (b) in order to obtain a narrower group of the compounds of formula (I), wherein X stands for a halogen;

$R_1$ means an acyl or substituted acyl group;

$R_2$, $R_3$ and $R_4$ represent hydrogen, or $R_2$ together with $R_3$ or $R_3$ together with $R_4$, respectively, form a chemical bond; and $R_5$ stands for a —$CH_2X$ group, wherein X is a halogen, a compound of the formula (II), wherein $R_1$ stands for hydrogen and $R_2$, $R_3$, $R_4$ and $R_5$ are as defined above or an acid addition salt thereof, or a crude mixture of ergot alkaloid bases containing several compounds of the formula (II), or a salt of this mixture is N-acylated or N-formylated and the thus-obtained N-acyl derivative is halogenated as described above under (a)

and, if desired, the compounds of the formula (I) obtained in any step of the above process (a) or (b) are separated from one another and, if desired, are converted to their acid addition salts.

The compounds of the formula (I) prepared by using the processes of the invention are partially known and partially new products which possess, on the one hand, valuable pharmacological effects and are, on the other hand, intermediates for the preparation of other pharmacologically active substances.

Thus, the compounds of the formula (I), wherein $R_1$ means hydrogen, an alkyl or an acyl group and $R_5$ is a hydroxymethyl or a $-CH_2-OR$ or a $CH_2X$ group, which are partially new halogenated lysergol or elymoclavine derivatives, show a very favorable neuroleptic and antihypoxic action. (Concerning the nomenclature: chemically, lysergol is 8-hydroxymethyl-6-methyl-9-ergolene and elymoclavine is 8-hydroxymethyl-6-methyl-8-ergolene.) The pharmacological action of the known compounds belonging to this group had first been described in an own former application (see the published European patent application No. 0,208,447). The compounds of the formula (I), wherein $R_1$ stands for hydrogen, a $C_{1-4}$ alkyl group or an acyl or substituted acyl group, $R_2$ together with $R_3$ or $R_3$ together with $R_4$ forms a chemical bond, respectively, and $R_5$ means a hydroxymethyl or $-CH_2-OR$ or $-CH_2X$ group (wherein R and X are as defined above), as well as their pharmacologic effects had first been described in our own Hungarian patent application No. 1719/86.

The compounds of the formula (I) containing a methyl group as $R_1$, hydrogen as $R_3$ and $R_4$, a methoxy group as $R_2$ and a $-CH_2-OR$ group as $R_5$, wherein R means a 5-bromonicotioyl group, are 2-halogenated nicergoline derivatives improving the cognitive function of the brain and showing an antihypoxic action. The pharmacological properties of the halogenated nicergoline derivatives and of the new 2chloro- and 2-iodonicergoline had first been described in our own Belgian patent specification No. 904,957.

Of the compounds of formula (I) containing hydrogen as $R_1$ and $R_4$ and a $-CO-NH-$(a) group as $R_5$, wherein $R_2$ L together with $R_3$ forms a chemical bond, the most valuable substance is 2-bromo-α-ergocryptine which is useful for the treatment of hyperprolactinaemia.

The other 2-halogenated ergoline derivatives of the formula (I), which can be prepared by using the novel process of the invention, are valuable intermediates for the preparation of pharmacologically active substances, such as the 2-halogenated nicergolines (2-halonicergolines), 2-bromo-α-ergocryptine and other compounds.

In the above-defined formulae:

X as halogen may be chlorine, bromine or iodine;

$R_1$ as a $C_{1-4}$ alkyl group may represent straight or branched chain groups such as a methyl, ethyl, n-propyl, isopropyl, n-butyl, secondary-butyl or tertiary-butyl group;

$R_1$ as an acyl group may stand for an aliphatic acyl group such as formyl, acetyl, propionyl, butyryl or hexanoyl group; or for an aromatic acyl group such as benzoyl or naphthoyl group; or for an aralkylacyl group such as phenylacetyl or 3-phenylpropionyl group; or for a heterocyclic acyl group such as picolyl, furoyl, nicotinoyl or isonicotinoyl group;

$R_1$ as a substituted acyl group may represent a ring-substituted aromatic or heterocyclic acyl group such as a trimethoxybenzoyl, 4-chlorobenzoyl, 2-chlorobenzoyl, 5-bromonicotinoyl or pyroglutamyl group;

$R_5$ as a $-CH_2-OR$ group may contain an acyl or substituted acyl group as R defined above as acyl groups for $R_1$.

The compounds of the formula (II) used as starting substances in the processes of the invention are partially known alkaloids of natural origin or can be prepared by methods known from the literature. Thus, lysergol of the formula (II), wherein $R_1$ stands for hydrogen, $R_2$ together with $R_3$ forms a chemical bond, $R_4$ means hydrogen and $R_5$ represents a hydroxymethyl group, can be prepared by plant extraction according to the British patent specification No. 1,398,997. Lysergol may also be prepared by the isomerisation of elymoclavine [Bull. Arg. Cem. Soc. Japan 20, 95 (1956); Helv. Chim. Acta 41, 1984 (1958)]. Elymoclavine of the formula (II), wherein $R_1$ stands for hydrogen, $R_3$ together with $R_4$ forms a chemical bond, $R_2$ means hydrogen and $R_5$ represents a hydroxymethyl group as well as the preparation thereof by fermentation had first been described in J. Agric. Chem. Soc. Japan, 25, 458 (1952). The derivatives containing hydrogen as $R_2$, $R_3$ and $R_4$ may be prepared by the hydrogenation of lysergol or elymoclavine, respectively, [(Y. Yamatodani S.: Bull. Agric. Chem. Soc. Japan, 19, 940 (1955)]. Agroclavine, wherein both $R_1$ and $R_2$ mean hydrogen, $R_3$ together with $R_4$ forms a chemical bond and $R_5$ stands for a methyl group, is a known natural alkaloid, which is similar to lysergol and elymoclavine, the preparation of which by fermentation had first been described by M. Abe et al. [J. Agric. Chem. Soc. Japan, 25, 458 (1952)].

The so-called "peptide alkaloids" wherein both $R_1$ and $R_4$ are hydrogen, $R_2$ together with $R_3$ forms a chemical bond and $R_5$ L represents a $-CO-NH-$(a) group, are also known ergot alkaloids (Albert Hofmann: "Die Mutterkornalkaloide", 1964). The dihydro derivatives of the "peptide alkaloids" containing hydrogen as $R_1$, $R_2$, $R_3$ and $R_4$ and a $-CO-NH-$(a) group as $R_5$ may be prepared by the hydrogenation of the natural peptide alkaloids, e.g. according to the process described in the U.S. Pat. No. 2,086,559.

Lysergic acid methyl ester of the formula (II), wherein both $R_1$ and $R_4$ are hydrogen, $R_2$ together with $R_3$ forms a chemical bond and $R_5$ represents a methoxycarbonyl group, was first prepared by esterifying lysergic acid with diazomethane (Smith and Timmis: J. Chem. Soc. 1936, 1440). The preparation of the dihydrolysergic acid derivative centaining hydrogen as $R_2$ and $R_3$ was first described by A. Stoll and A. Hofmann [Helv. Chim. Acta 31, 635 (1946)].

1-Methyllumilysergol of the formula (II), wherein $R_1$ stands for a methyl group, $R_2$ represents a methoxy group, $R_3$ and $R_4$ l are hydrogen and $R_5$ means a hydroxymethyl group, and the preparation thereof were described in the European patent specification No. 0,004,664.

Nicergoline of the formula (II), containing a $-CH_2-OR$ group as $R_5$, wherein R stands for a 5-bromonicotinoyl group, is a known peripheral vasodilator first described in the U.S. Pat. No. 3,228,943.

The preparation of 1-methyllysergol and 1-methylelymoclavine, respectively of the formula (II), containing a methyl group as $R_1$ and a hydroxymethyl group as $R_5$ were described in the following literature references: E. Eich: Archiv. Pharm. 316, 718 (1983); and J. Smidrkal and M. Semansky: Collect. Czech. Chem. Comm. 47, 6220 (1982).

8-Acyllysergol and 8-acylelymoclavine derivatives, respectively containing hydrogen as $R_1$ and a $-CH-$ 2—OR group as $R_5$, were described in the Belgian patent specification No. 753,635.

The starting materials of the formula (II) containing hydrogen as $R_1$ and a —$CH_2X$ group as $R_5$ may be prepared as described in Collect. Czech. Chem. Comm. 39, 2819 (1969).

Finally, the novel diacyl derivatives of the formula (II), containing an acyl or substituted acyl group as $R_1$ and a —$CH_2$—OR group as $R_5$, can be prepared by the diacylation of lysergol or elymoclavine, respectively. For this purpose lysergol or elymoclavine, respectively is acylated by using a carboxylic acid derivative suitable for acylation such as the acid anhydride, acyl halide or ketene, preferably by using an acyl halide in a known manner. On carrying out the acylation with an acyl halide, an apolar aprotic solvent such as a chlorinated hydrocarbon, e.g. chloroform, carbon tetrachloride or dichloromethane or an aromatic hydrocarbon, e.g. benzene or toluene, is used between room temperature and the boiling point of the solvent employed, in the presence of an acid binding agent and a cayalyst.

In the processes of the invention, pure ergoline derivatives may be used as starting substances; however, the processes of the invention can also be used when a so-called crude alkaloid mixture containing a number of ergoline alkaloids or the salts thereof are used as starting materials.

In the case of compounds of the formula (II) containing a —CO—NH—(a) group or a methoxycarbonyl group as $R_5$, the "inine" diastereomeric form is also possible. When these compounds are used as starting materials, then the appropriate halogenated "inine" compounds of the formula (I) are obtained which are then transformed (converted) to the appropriate "ine" forms.

Concerning the novel, pharmacologically active compounds of the formula (I) obtained by using the processes of the invention, the compositions containing these compounds or the acid addition salts thereof as active ingredients as well as the process for the preparation of these pharmaceutical compositions are also within the scope of the invention.

The halogenation of ergot alkaloids in 2-position had first been described by F. Toxler and A. Hofmann [Helv. Chim. Acta, 40, 2160 (1957)]. These authors halogenated the so-called peptide alkaloids with N-halosuccinimide.

According to the Belgian patent specification No. 858,633, clavine-type alkaloids were chlorinated by using thionyl chloride and a boron trifluoride etherate complex.

The halogenation of clavine alkaloids and preparation of new 2-halogenated clavine derivatives were described in our own Hungarian patent specification No. 190,920 and in the published European patent application No. 0,208, 447, according to which the chlorination is carried out by using dimethylsulfoxide saturated with gaseous hydrogen chloride or with tertiary-butyl hypochlorite in anhydrous tetrohydrofuran; the bromination or iodination, resepectively is accomplished by elemental bromine or iodine, respectively, or N-bromosuccinimide or N-iodosuccinimide, respectively.

Of the compounds of formuly (I) halogenated in the 2-position of the ergoline skeleton, a commonly known, therapeutically active drug is 2-bromo-60-ergocryptine containing a —CO—NH—(a) group as $R_5$, wherein R' stands for an isopropyl group and R" means an isobutyl group, both $R_1$ and $R_4$ are hydrogen, $R_2$ and $R_3$ together form a chemical bond and X is a bromine. For the preparation of 2-brom-α-ergocryptine, a number of processes are known.

The preparation of 2-bromo-α-ergocryptine was first described in the Swiss patent specification No. 507,249, according to which α-ergocryptine was brominated. This reaction is carried out by using a mild brominating agent, e.g. N-bromophthalimide, N-bromosuccinimide, N-bromocarprolactam or a dioxane-bromine complex in an inert solvent at a temperature between 10° C. and 80° C. Suitable inert, apolar solvents are e.g. dioxane, acetonitrile and dichloromethane. The duration of the brominating reaction varies between 70 minutes and 6 hours. Although the brominating agent is used in a large excess it was observed in our own reproduction experiments that the reaction is not selective and a part of the starting material remains unchanged. In addition, this brominating reaction is accompanied by a high number of decomposition products, whereby unidentifiable, dark and partially tarry products are formed. The unchanged starting substance and the side product should be separated from 2-bromo-α-ergocryptine by column chromatography. The removal of the large volume of the solvent is a tedious procedure, whereby the product becomes more colored. No yield is given in this patent specification; according to our own measurements, the amount of the unchanged α-ergocryptine varies between 20 and 30%.

According to the German patent specification No. 2,752,532, α-ergocryptine is brominated under an inert gas, e.g. nitrogen, by using pyrrolidone dibromide hydrobromide or N-bromosaccharine in a cyclic ether, in the presence of a radical initiator at room temperature or at a somewhat higher temperature. From the crude reduction product, the brominated compound can only be isolated by column chromatography by using a specific adsorbent. The bromination is carried out between 55° C. and room temperature. The reaction lasts 30 minutes at 50° C., the reaction mixture should, however, be kept at room temperature for 2 days in order to complete the reaction. According to the examples of this patent specification the yield amounts to 78 to 87%. These yields could not be reproduced in our own reproduction experiments: namely, though the starting α-ergocryptine is consumed in the reaction, 20 to 30% of an unknown side product and 5 to 10% of 2-bromo-α-ergocryptinine are, however, formed in addition to the desired 2-bromo-α-ergocryptine. These compounds can only be separated from 2-bromo-α-ergocryptine by using the above-mentioned particular chromatography.

Summing up, a common disadvantage of the above-reported processes consists in that the disclosed reaction times are long, the yield of the desired brominated product is not quantitative and the product obtained must be purified by using column chromatography which can only be realized with high difficulties on an industrial scale.

A more advantageous process was described for the preparation of 2-bromo-α-ergocryptine in our Belgian patent specification 904,897, according to which α-ergocryptine is brominated in anhydrous dimethylsulfoxide, by using gaseous hydrogen bromide at room temperature. On comparison to the processes known up to the present, this bromination proceeds within a much shorter time and selectively in the 2-position of the ergoline skeleton.

The disadvantage of this process, giving very good yields in the laboratory, consists in that an equipment with a particular sealing and material is required on the industrial scale; namely, the reaction is rather aggressive as a consequence of the strongly acid medium.

An other difficulty of this process consists in that the bromination can only be accomplished in high yields under a defined water content; in the presence of a water content higher than this limit the selective brominating reaction is overshadowed by an undesired oxidation reaction. Thus, when the bromination is carried out in large volumes, the realisation of the reaction under preferable conditions, requiring removing the water arising in the reaction as well as the water present in the system, requires supplementing equipment and technological operations making very difficult the carrying out of this reaction which can simply be accomplished on a low scale.

The aim of the present invention is to elaborate a selective halogenating process which can more preferably be used for the halogenation in 2-position of the ergoline skeleton as compared to the halogenating processes of the prior art.

According to the novel process of the present invention, the ergoline derivatives are selectively halogenated by using a novel halogenating system consisting of dimethylsulfoxide, a trialkylhalosilane or a triarylhalosilane and optionally a hydrogen halide. In the literature, no reference was found, according to which a carbon-halogen bond was formed directly from a carbon-hydrogen bond by using a trialkylhalosilane or a triarylhalosilane compound.

It is known that the above-mentioned halosilanes can be used in the sugar chemistry for the formation of a carbon-halogen bond by cleaving of a previously formed acetoxy group [Chem. Ber. 113, 3075 (1980)]. In this reference, trimethyliodosilane and trimethylbromosilane were also used. Inert solvents, e.g. toluene, were used in this reaction, which lasts several hours and requires a high temperature, e.g. about 80° C.

According to the U.S. Pat. No. 3,992,422, steroids are chlorinated or brominated by using a trialkylchlorosilane or a triarylbromosilane, respectively. The carbon-halogen bond is built up by cleaving the previously formed acyl derivative.

According to J. W. Gillard and M. Israel (Tetrahedron Letters, 22, 513) anomeric glycosyl acetates are brominated with trimethylbromosilane. In this reaction, the carbon-halogen bond is also formed after cleaving a carbon-oxygen bond.

According to the process of the present invention, the ergoline derivatives are selectively halogenated in the 2-position, where a carbon-halogen bond is directly formed from a carbon-hydrogen bond. The halogenation is carried out by using excess dimethylsulfoxide as calculated for the trialkylhalosilane or triarylhalosilane used, and optionally by using a hydrogen halide. In this reaction, dimethylsulfoxide can not be considered as an inert solvent. Suitable trialkylhalosilanes are e.g. trimethylchlorosilane, triethylchlorosilane, tri(n-propyl)chlorosilane, tri(n-butyl)chlorosilane or -bromosilane or -iodosilane, respectively, preferably trimethylchlorosilane, trimethylbromosilane or trimethyliodosilane; as a triarylhalosilane e.g. triphenylchlorosilane, triphenylbromosilane or triphenyliodosilane can be used. Suitable hydrogen halides are hydrogen chloride, hydrogen bromide or hydrogen iodide in amounts of about 0.1 to 1 equivalent as calculated for the moles of the starting alkaloid. On using these reagents, the selectivity of the halogenating reaction is higher and the rate of the reaction is increased.

As compared to the above-reported processes of the prior art, the process of the invention is extraordinarily preferable: the halogenation proceeds at room temperature within a very short period, i.e. during 5 to 20 minutes; the halogenating system used provides very mild reaction conditions; thus, no specific equipment is required for carrying out the reaction. A further great advantage of the process of the invention is that it is far less sensitive to the water content of dimethylsulfoxide which is particularly preferable from the view-point of the industrial utilisation.

The halogenating reaction of the invention, which is highly selective and free of side reactions, proceeds with a yield of 90 to 95%; thus, the working-up and purification of the reaction mixture are simple and do not need any chromatographic separation which cannot be avoided on using the processes of the prior art.

The process of the invention is described in detail in the following.

In process (a) of the invention, the appropriate ergoline derivatives of the formula (II) or the acid addition salts thereof or a crude alkaloid mixture containing several ergoline derivatives of formula (II) or the acid addition salts thereof, used as starting materials are halogenated and after isolation the thus-obtained appropriate halogenated ergoline derivatives are, if desired, (i) N-acylated or N-formylated; or
(ii) esterified; or
(iii) hydrolyzed.

In process (b) of the invention, the appropriate ergoline derivatives of the formula (II) or the acid addition salts thereof or a crude alkaloid mixture containing several ergoline derivatives of formula (II) or the acid addition salts thereof used as starting materials are N-acylated or N-formylated, whereupon the thus-obtained N-acyl or N-formyl derivatives are halogenated as described above under (a) and, if desired, the compounds of the formula (I) obtained in any step of the above processes (a) or (b) are converted to their acid addition salts.

In the processes according to the invention, the halogenation is carried out at room temperature in the following way.

To the dimethylsulfoxide, 6 to 12 equivalents of one of the above trialkylhalosilane or triarylhalosilane compounds are added as calculated for the number of moles of the starting alkaloid or alkaloid mixture. The reaction mixture is stirred under an inert gas, e.g. under nitrogen or argon, for 5 to 15 minutes. Then, the solution of the starting material in dimethylsulfoxide is added to the above mixture and stirred for 5 to 20 minutes. In the case when a hydrogen halide is also used in the halogenating process, an amount of about 0.1 to 1 equivalent of the appropriate gaseous hydrogen halide, as calculated for the number of moles of the starting alkaloid or alkaloid mixture, is absorbed in dimethylsulfoxide and the thus-obtained solution is added to the solvent before adding the trialkylhalosilane or triarylhalosilane. After the termination of the reaction, which is controlled by thin layer chromatography, the mixture is poured into water, the pH value of the mixture is adjusted to 8–9 by adding a base, e.g. sodium hydroxide, sodium hydrogen carbonate or ammonium hydroxide, preferably ammonium hydroxide, and then the product is extracted into a water-immiscible organic solvent such as a chlorinated hydrocarbon or an aromatic hydrocarbon, preferably dichloromethane. The organic phase is dried over anhydrous sodium or magnesium sulfate and evaporated. If necessary, the residue is purified by recrystallization or chromatography.

The N-acylation can be accomplished by using an acid anhydride, acyl halide or ketene, preferably an acyl halide.

On using an acid anhydride for the N-acylation, the reaction is carried out at a temperature higher then room temperature, preferably at a temperature between 40° C. and the boiling point of the solvent used. An excess of the acid anhydride or a mixture of the acid anhydride and the appropriate acid can be used as solvent. As catalysts, inorganic salts commonly used for the acylation of indole derivatives, preferably magnesium perchlorate, may be employed.

On using an acyl halide for the N-acylation, the reaction is carried out in an apolar aprotic solvent commonly used for the acylation with acyl halides. Suitable apolar aprotic solvents are e.g. chlorinated hydrocarbons such as chloroform, carbon tetrachloride or dichloromethane; or aromatic hydrocarbons such as benzene or toluene. Preferably, dichloromethane is used. The reaction is accomplished at a temperature between room temperature and the boiling point of the solvent used, preferably at room temperature. As acid binding agent a base, e.g. sodium hydroxide, potassium hydroxide, diethylamine or triethylamine, preferably potassium hydroxide, is used. Suitable catalysts are the tetraalkylammonium salts, preferably tetrabutylammonium hydrogen sulfate.

The N-acylation using ketene is carried out in a known manner, e.g. as described in Helv. Chim. Acta 40, 1706 (1957).

A compound of the formula (I) containing hydrogen as $R_1$ can be transformed to the appropriate derivative containing a formyl group as $R_1$ by reacting with a formylating agent. This formylation can be carried out in a known manner, preferably e.g. by using Vilsmeier's formylation process, according to which a formamide derivative such as N-methylformanilide or dimethylformamide is used together with phosgene or phosphorus oxychloride; preferably dimethylformamide and phosphorus oxychloride are used. As solvent an apolar aprotic liquid, e.g. benzene or chlorobenzene, or, preferably, an excess of dimethylformamide is employed. The reaction is accomplished at a temperature between 60° C. and 80° C.

The derivatives containing a hydroxymethyl group as $R_5$ obtained according to the process (a) (ii) are esterified in two steps. In the first step, an active ester is prepared, whereupon the esterification is carried out by using this active ester in the second step.

The active ester is prepared in such a way that N-hydroxysuccinimide is dissolved in an aprotic solvent, e.g. tetrahydrofuran or ethyl acetate, and first the appropriate acid in excess and then N,N-dicyclohexylcarbodiimide in a molar equivalent amount as calculated for N-hydroxysuccinimide are added. The precipitate obtained after stirring at room temperature is filtered off, then the mother liquor is evaporated under reduced pressure. The thus-obtained active ester is a white, amorphous product which is recrystallized, if necessary, from ethanol.

In the second step, the esterification with the active ester is carried out at 20° to 60° C., preferably at room temperature in an aprotic solvent such as tetrahydrofuran, benzene or actonitrile, preferably in tetrahydrofuran, in the presence of an organic base, e.g. triethylamine or pyridine, preferably in the presence of pyridine. An excess of the organic base used in the esterification may also serve as a solvent. The ergoline derivative to be esterified is dissolved in the appropriate solvent or in the pure organic base and then the active ester prepared as described above is added. The reaction is followed by thin layer chromatography. After completion of the esterification, the solvent is removed under reduced pressure, the product is separated from the organic base by extraction and after drying and evaporation under reduced pressure, the product is recrystallized from diethyl ether.

On using 1-methyllumilysergol as starting substance and 5-bromonicotinic acid in the preparation of the active ester, nicergoline is obtained.

The hydrolysis of a derivative obtained according the process (a) (ii), containing e.g. a methoxycarbonyl group as $R_5$, is accomplished in a known way, in an aqueous-alcoholic alkaline solution, preferably in an aqueous-ethanolic solution of potassium hydroxide, at a temperature between room temperature and the boiling point of the solvent used.

The compounds of the formula (I) obtained by using the processes (a) or (b) of the invention may be separated in such a way that the catalyst is filtered off from the reaction mixture, the thus-obtained solution is evaporated, the residue is mixed with a water-immiscible organic solvent such as dichloromethane, chloroform, dichloroethane, benzene or toluene, and then, if desired, made alkaline, preferably by using an 5% aqueous sodium carbonate solution, the organic phase is separated, washed with water, dried and evaporated. If desired, the crude product obtained as an evaporation residue is purified by recrystallization.

In the case of starting substances of the formula (II), wherein $R_5$ stands for a —CO—NH—(a) group or a carboxyl group, an "inine" diastereomeric form can occur. When in the process (a) an "inine" diastereomeric form or a crude alkaloid mixture possibly containing the "inine" form in addition to the "ine" form is used as starting material, then the halogenated "inine" derivatives can be converted to the therapeutically active "ine" form by epimerization in an acidic medium as follows.

The mixture of the 2-halogenated ine and inine bases or a mixture of various 2-halogenated inine bases is dissolved in a mixture containing acetone and methanol, then glacial acetic acid and phosphoric acid are added to this homogeneous solution. Then, the reaction mixture is warmed and after standing overnight, the precipitated "2-halo-ine" crystals are filtered off and washed with acetone. The mother liquor together with the acetone washing solution is evaporated under reduced pressure, the residue is dissolved in 5% tartaric acid solution, clarified with activated carbon, filtered and the pH value of the solution is adjusted to 8–9 by adding ammonium hydroxide. The precipitated "2-halo-inine" base or mixture of bases is filtered off, washed with water, dried and subjected to a second epimerization as described above. This epimerization may be repeated several times and, of course, it may also be carried out before the halogenation.

The base is liberated from the phosphate salt of the "2-halo-ine" form as follows. The salt is dissolved in a mixture containing acetic acid, acetone and water and the pH value of the solution is adjusted to 8–9 by adding potassium hydroxide solution. The 2-halo-ine base is isolated by extraction with dichloromethane.

When a crude alkaloid mixture or a salt thereof is used as starting material, the obtained mixture of 2-halogenated alkaloids is isolated in the base form. The desired 2-halogenated alkaloid is separated from the other accompanying 2-halogenated alkaloid derivatives by using chromatography.

The compounds of the formula (I) obtained in any reaction step of the above processes (a) or (b) of the invention may be converted, if desired, to their acid addition salts. This salt formation can be performed in an inert solvent, e.g. in a $C_{1-6}$ aliphatic alcohol or in a dipolar aprotic solvent, e.g. ether or acetone, in such a manner that the base of the formula (I) is dissolved in the solvent and the appropriate acid or a solution of this acid in the same solvent is added to the above solution until the pH value of the mixture becomes mildly acidic. The precipitated acid addition salt is separated from the reaction mixture in a suitable manner, e.g. by filtration.

The new active ingredients of the formula (I), wherein $R_1$ stands for a methyl or acyl group, $R_2$ together with $R_3$ forms a chemical bond and $R_4$ is hydrogen, or $R_3$ together with $R_4$ forms a chemical bond, $R_2$ stands for hydrogen and $R_5$ represents a —$CH_2$—OR or —$CH_2X$ group, can be converted into pharmaceutical compositions by mixing them with the usual non-toxic, inert, solid or liquid carriers and/or auxiliary agents which are commonly used in compositions for enteral or parenteral administration. As carriers e.g. water, gelatine, lactose, starch, pectin, magnesium stearate, stearic acid, talc, and vegetable oils such as peanut oil or olive oil or the like can be employed. The active ingredient can be formulated to the usual pharmaceutical compositions, particularly to solid forms such as rounded or angled tablets, dragées, capsules, e.g. gelatine capsules, pills, suppositories or the like. The amount of the solid materials can vary between wide limits, preferably they are used in an amount between about 25 mg and 1 g. The compositions may optionally contain the commonly used pharmaceutical additives, e.g. preserving agents, stabilizers, wetting agents, emulsifying agents or the like.

The pharmaceutical compositions of the invention can be prepared by using the common methods, e.g. in the cases of solid compositions by sieving, mixing, granulating and compressing the components. The compositions may be subjected to further operations, e.g. sterilization, commonly used in the phrmaceutical industry.

The invention is illustrated in detail by the aid of the following non-limiting Examples.

EXAMPLE 1

Preparation of 2-bromolysergol
(2-bromo-8-hydroxymethyl-6-methyl-9-ergolene)

2 g of trimethylbromosilane are portionwise added to 20 ml of dimethylsulfoxide and the reaction mixture is stirred at room temperature for 15 minutes, then a solution containing 1 g of lysergol in 15 ml of dimethylsulfoxide is added. After stirring for 20 minutes, the mixture is poured onto 150 ml of ice-water and the pH is adjusted to 8-9 by adding aqueous ammonia. The mixture is extracted 3 times with 30 ml of dichloromethane each. The combined organic phase is washed 3 times with 20 ml of 10% sodium chloride solution each, dried over sodium sulfate, filtered and the filtrate is evaporated under reduced pressure to give the title compound in a yield of 0.8 g (0.00277 mole, 70.5%), m.p.: 193° C.

UV (MeOH) $\lambda_{max}$=310 nm.

$^1$H-NMR (DMSO+CDCl$_3$, δppm): 2.48 (s, 3H; N—CH$_3$), 3.60 (d, 2H; CH$_2$—OH), 6.30 (s, 1H; olefinic), 6.95 (s, 3H; arom. H).

IR (KBr), cm$^{-1}$: 3160 (indole-NH); 780 (arom. deform.).

EXAMPLE 2

Preparation of 2-bromoelymoclavine
(2-bromo-8-hydroxymethyl-6-methyl-8-ergolene)

The process described in Example 1 is followed, except that 1 g of elymoclavine is used as starting material to give the title compound in a yield of 0.76 g (0.0026388 mole, 68.2%), m.p.: 216° C.

UV (MeOH) $\lambda_{max}$=287 nm.

$^1$H-NMR (DMSO, δppm): 2.55 (s, 3H; N—CH$_3$), 3.95 (s, 2H; CH$_2$OH), 6.18 (s, 1H; olefinic), 6.89 (m, 3H; arom. H).

IR (KBr), cm$^{-1}$: 3180 (indole-NH); 780 (arom. deform.).

EXAMPLE 3

Preparation of 2-chlorolysergol
(2-chloro-8-hydroxymethyl-6-methyl-9-ergolene)

1 g of lysergol is halogenated according to the process of Example 1, except that 1.7 g of trimethylchlorosilane are used instead of trimethylbromosilane. The product is isolated as described in Example 1. The yield of the title compound is 0.73 g (0.0025347 mole, 64.4%), m.p.: 207° C.

$^1$H-NMR (CDCl$_3$+DMSO-d$_6$, δppm): 2.45 (s, 3H; N—CH$_3$), 3.55 (d, 2H; CH$_2$-OR), 6.25 (s, 1H; olefinic), 6.97 (s, 3H; arom. H).

IR (KBr), cm$^{-1}$: 3160 (indole-NH); 1610 (arom. nucleus): (arom. deform.).

EXAMPLE 4

Preparation of 2-chlorolysergol phosphate
(2-chloro-8-hydroxymethyl-6-methyl-9-ergolene phosphate)

To 20 ml of dimethylsulfoxide 6 ml of a solution containing hydrogen chloride in dimethylsulfoxide, prepared by absorbing 0.6 equivalent of hydrogen chloride as calculated for the mole number of the compound to be halogenated, are added, then 1.7 g of trimethylchlorosilane are added under stirring and the reaction mixture stirred for an additional 15 minutes. After the portionwise addition of 1.4 g of lysergol phosphate, the mixture is stirred at room temperature for 10 minutes, then poured into 5 volumes of saturated aqueous sodium chloride solution and made alkaline by adding aqueous ammonia up to a pH value of 8 to 9. The precipitate is filtered off, washed twice with 10 ml of water each, then the thus-obtained product is dissolved in 50 ml of 4% aqueous phosphoric acid solution at 50° C. After cooling the solution to room temperature, the title compound begins to separate. The precipitate is filtered off, washed with water and dried to give the title phosphate salt in a yield of 1.2 g (0.0031 mole, 78.9%), m.p.: 248° C.

EXAMPLE 5

Preparation of 2-bromolysergol
(2-bromo-8-hydroxymethyl-6-methyl-9-ergolene)

The process described in Example 4 is followed by using 1 g of lysergol phosphate as starting material. The bromination is carried out by using a mixture of 0.4 equivalents of hydrogen bromide, as calculated for the starting material, absorbed in dimethylsulfoxide and 2.2 ml of trimethylbromosilane to give the title compound in a yield of 1.0 g (0.00233 mole, 82%). The physical characteristics of this product are identical with those of the product of Example 1.

EXAMPLE 6

Preparation of 2-chloroelymoclavine
(2-chloro-8-hydroxymethyl-6-methyl-8-ergolene)

The process described in Example 3 followed, except that 1 g of elymoclavine is used as starting material to give the title compound in a yield of 0.61 g (0.002119 mole, 53.79%), m.p.: 199° C.

$^1$H-NMR (CDCl$_3$+DMSO-d$_6$, $\delta$ppm): 2.45 (s, 3H; N—CH$_3$), 3.95 (s, 2H; CH$_2$—OH), 6.24 (s, 1H; olefinic), 6.89 (m, 3H; arom. H).

IR (KBr): cm$^{-1}$: 3180 (indole-NH), 780 (arom. deform.).

EXAMPLE 7

Preparation of 2-iodolysergol
(8-hydroxymethyl-2-iodo-6-methyl-9-ergolene)

2.3 g of trimethyliodosilane are portionwise added to 20 ml of dimethylsulfoxide and the mixture is stirred at room temperature for 5 minutes. Then, a solution of 1 g of lysergol in 15 ml of dimethylsulfoxide is added, the reaction mixture is stirred for 15 minutes, then poured into water and made alkaline by adding aqueous ammonia up to a pH value of 8 to 9. The precipitate is filtered off, wash 3 times with 20 ml of water each and dried to give the title compound in a yield of 1.1 g (0.002913, mole, 74%).

$^1$H-NMR (CDCl$_3$+DMSO-d$_6$, $\delta$ppm): 2.46 (s, 3H; N—CH$_3$), 3.97 (s, 2H; CH$_2$—OH), 6.29 (s, 1H; olefinic), 6.96 (m, 3H; arom. H).

IR (KBr): cm$^{-1}$: 3160 (indole-NH); 1610 (arom. skeleton).

EXAMPLE 8

Preparation of 1-methylelymoclavine
(1,6-dimethyl-8-hydroxymethyl-8-ergolene)

The suspension of 0.8 g of finely powdered potassium hydroxide in 6 ml of dimethylsulfoxide is stirred for 10 minutes, then 1 g of elymoclavine is portionwise added and the mixture is stirred at 15° to 20° C. for 45 minutes. After the portionwise addition of 0.25 ml of methyl iodide, the mixture is stirred at 25° to 30° C. for additional 45 minutes and then poured into 150 ml of ice-water. The precipitate is filtered off, washed 3 times with 10 ml of water each, dried and subjected to chromatography on a column prepared from a 15-fold amount of Kieselgel by using an 8:2 mixture of chloroform and methanol. After recrystallization from acetone, the title compound is obtained in a yield of 0.6 g (0.0022 mole, 56%), m.p.: 210°–211° C.

EXAMPLE 9

Preparation of 1-methyllysergol
(1,6-dimethyl-8-hydroxymethyl-9-ergolene)

1 g of lysergol is methylated and the obtained product is isolated by using the process of Example 8 to give the title compound in a yield of 0.65 g (0.00236 mole 60%), m.p.: 216°–217° C.

EXAMPLE 10

Preparation of 2-chloro-1-methyllysergol maleate
(2-chloro-1,6-dimethyl-8-hydroxy-methyl-9-ergolene maleate)

1.7 g of trimethylchlorosilane are portionwise added to 20 ml of dimethylsulfoxide, the mixture is stirred at room temperature for 15 minutes, then a solution of 1 g of 1-methyllysergol in 15 ml of dimethylsulfoxide is dropwise added. After stirring for 15 minutes, the reaction mixture is poured into 150 ml of ice-water and made alkaline by adding aqueous ammonia up to a pH value of 8 to 9. The precipitate is filtered off, washed 3 times with 20 ml of water each, dried and purified by chromatography on a column prepared from a 15-fold amount of Kieselgel by using an 8:2 mixture of chloroform and methanol as eluant. The title maleate salt is precipitated from methanol and obtained in a yield of 1.17 g (0.00280 mole, 75,7%), m.p.: 205°–209° C.

$^1$H-NMR (DMSO-d$_6$, $\delta$ppm): 3.05 (s, 3H; N—CH$_3$), 3.55 (s, 2H; CH$_2$OH), 3.72(s, 3H; indole N—CH$_3$), 6.07 (s, 2H; olefinic, maleic acid), 6.58 (s, 1H; olefinic), 7.21 (m, 3H; indole).

IR (KBr), cm$^{-1}$: 3550–3100 (OH); 2800–2800 (protonated nitrogen), 1700–1530 (CO$^-$), 1582 (arom. skeleton), 783 (arom. deform.).

EXAMPLE 11

Preparation of 2-chloro-1-methylelymoclavine
(2-chloro-1,6-dimethyl-8-hydroxymethyl-8-ergolene)

1 g of 1-methylelymoclavine is chlorinated according to the process of Example 10 and the thus-obtained product is recrystallized from methanol to give the title compound in a yield of 0.79 g (0.00258 mole, 69.2%), m.p.: 186°–189° C.

$^1$H-NMR (DMSO-d$_6$, $\delta$ppm): 2.31 (s, 3H; N—CH$_3$), 3.63 (s, 3H; indole N—CH$_3$), 3.98 (s, 2H; CH$_2$—OH); 6.29 (s, 1H; olefinic), 7.15 (m, 3H; arom. H).

IR (KBr), cm$^{-1}$: 2820 (indole N—CH$_3$); 1607 (arom. skeleton), 780 (arom. deform.).

EXAMPLE 12

Preparation of 8-acetyloxymethyl-6-methyl-9-ergolene 1 g of lysergol is dissolved in 5 ml of acetic acid and after adding 15 ml of glacial acetic acid, the mixture is stirred at room temperature for 2 hours. After completion of the reaction, the mixture is diluted with the 5-fold volume of water and made alkaline by adding aqueous ammonia up to a pH value of 7 to 7.5 under ice cooling. The mixture is extracted 3 times with 20 ml of chloroform each. The combined organic phase is extracted with 20 ml of water, dried and evaporated under reduced pressure to give the title compound in a yield of 1.1 g (0.00374 mole, 95%).

$^1$H-NMR (CDCl$_3$, $\delta$ppm): 2.1

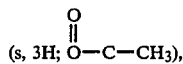

2.55 (s, 3H; N—CH$_3$), 4.05 (s, 2H; CH$_2$—O—), 6.41 (s, 1H; olefinic), 7.12 (m, 4H; arom.).

IR (KBr), cm$^{-1}$: 2780 (aliphatic next to nitrogen); 1730 (ester carbonyl); 1260 (ester C—O—C); 1600–1575 (arom. nucleus).

EXAMPLE 13

Preparation of 8-acetyloxymethyl-6-methyl-8-ergolene 1 g of elymoclavine is acetylated and the product isolated by using the process of Example 12 to give the title compound in a yield of 1.08 g (0.00366 mole, 93%).

$^1$H-NMR (CDCl$_3$, δppm): 2.05

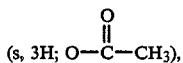

2.45 (s, 3H; N—CH$_3$), 4.55 (s, 2H; —CH$_2$—O), 7.35 (s, 4H; arom).

IR (KBr), cm$^{-1}$: 2780 (aliphatic next to nitrogen); 1725 (ester carbonyl); 1250 (ester C—O—C); 1600–1570 (arom. nucleus).

EXAMPLE 14

Preparation of 8-acetyloxymethyl-2-chloro-6-methyl-9-ergolene 2.0 ml of trimethylchlorosilane are portionwise added to 20 ml of dimethylsulfoxide under stirring. After stirring for 15 minutes, a solution of 1 g of 8-acetyloxymethyl-6-methyl-9-ergolene in 5 ml of dimethylsulfoxide is added, then the mixture is stirred at room temperature for 20 minutes and then poured into 140 ml of water. The pH value is adjusted to 8 to 9 by adding aqueous ammonia and the mixture is extracted 3 times with 30 ml of dichloromethane each. The combined organic phase is dried over anhydrous sodium sulfate, filtered off and evaporated to dryness under reduced pressure. The residue is purified by chromatography on a Kieselgel column by using a 7:3 mixture of benzene and acetone as eluant. After recrystallization of the isolated product from diethyl ether, the title compound is obtained in a yield of 0.8 g (0.0025 mole, 71%).

$^1$H-NMR (CDCl$_3$, δppm): 2.05 (s, 3H; —O—C—CH$_3$); 2.60 (s, 3H; N—CH$_3$); 4.05 (s, 2H; CH$_2$—O—); 6.51 (s, 1H; olefinic); 7.2 (m, 3H; arom.).

IR (KBr), cm$^{-1}$: 2780 (aliphatic next N); 1720 (ester carbonyl); 1263 (ester C—O—C).

EXAMPLE 15

Preparation of 8-acetyloxymethyl-2-chloro-6-methyl-8-ergolene 1 g of 8-acetyloxymethyl-6-methyl-8-ergolene is halogenated and the product is isolated by using the process of Example 14 to give the title compound in a yield of 0.75 g (0.00234 mole, 67%).

$^1$N-NMR (CDCl$_3$, δppm): 2.15

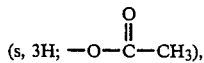

2.6 (s, 3H; N—CH$_3$), 4.65 (s, 2H; CH$_2$—O—), 7.31 (m, 3H; arom.).

IR (KBr), cm$^{-1}$: 1726 (ester carbonyl); 1256 (ester C—O—C).

EXAMPLE 16

Preparation of 8-acetyloxymethyl-2-bromo-6-methyl-9-ergolene 1 g of 8-acetyloxymethyl-6-methyl-9-ergolene is reacted with 3.2 ml of trimethylbromosilane by using the process of Example 14. The reaction mixture is worked up and the product is isolated by using the process of Example 13.

$^1$H-NMR (CDCl$_3$, δppm): 2.2

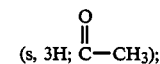

2.65 (s, 3H; N—CH$_3$); 4.15 (s, 2H; CH$_2$—); 6.60 (s, 1H; olefinic); 7.2 (m, 3H; arom.).

IR (KBr), cm$^{-1}$: 1730 (ester carbonyl); 1260 (ester C—O—C).

EXAMPLE 17

Preparation of 1-acetyl-8-acetyloxymethyl-6-methyl-9-ergolene

To the solution of 1.5 g of lysergol in 300 ml of anhydrous dichloromethane first 4.8 g of powdered potassium hydroxide, then 1.28 g of tetrabutylammonium sulfate and finally 6.6 ml of acetyl chloride are added under stirring. The reaction mixture is stirred at room temperature for an additional 3 hours, the insoluble part is filtered off and the solution is washed twice with 60 ml of saturated aqueous sodium hydrogen carbonate solution each. The title compound is isolated by chromatography on a Kieselgel column by using a 7:3 mixture of benzene and acetone as eluant in a yield of 1.1 g (0.00325 mole, 55%).

$^1$H-NMR (CDCl$_3$, δppm): 2.1

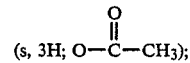

2.55 (s, 3H; N—CH$_3$), 2.8

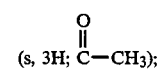

4.05 (s, 2H; CH$_2$—O—), 6.41 (s, 1H; olefinic), 7.15 (m, 4H; arom.).

IR (KBr), cm$^{-1}$: 2790 (aliphatic next to N); 1730 (ester carbonyl); 1690 (acid amide carbonyl); 1260 (ester C—O—C).

EXAMPLE 18

Preparation of 1-acetyl-8-acetyloxymethyl-6-methyl-8-ergolene

The process of Example 17 is followed, except that 2 g of elymoclavine is used as starting material to give the title compound in a yield of 1.6 g (0.0047 mole, 60%), m.p.: 149°–150° C.

$^1$H-NMR (CDCl$_3$, δppm): 2.1

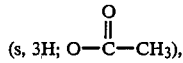

2.45 (s, 3H; N—CH₃), 2.78

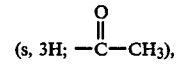

4.48 (s, 2H; —CH₂—O), 6.43 (s, 1H; olefinic), 7.13 (m, 4H; arom.).

IR (KBr), cm⁻¹: 2780 (aliphatic next to N); 1726 (ester carbonyl); 1695 (acid amide carbonyl); 1260 (ester C—O—C); 1605–1780 (arom. nucleus); 780 (arom. deform.).

EXAMPLE 19

Preparation of 1-acetyl-8-acetyloxymethyl-2-chloro-6-methyl-9-ergolene 1.9 g of trimethylchlorosilane are dropwise added to 20 ml of dimethylsulfoxide while stirring. After stirring for 15 minutes, a solution of 1 g of 1-acetyl-8-acetyloxymethyl-6-methyl-9-ergolene in 5 ml of dimethylsulfoxide is added, the mixture is stirred at room temperature for 25 minutes and then poured into 140 ml of water. The pH value of the mixture is adjusted to 8 to 9 by adding aqueous ammonia and extracted 3 times with 30 ml of dichloromethane each. The organic phase is dried over anhydrous sodium sulfate, filtered and evaporated to dryness under reduced pressure. The residue is purified by chromatography on a Kieselgel comumn by using a 7:3 mixture of benzene and acetone. After recrystallization of the product from diethyl ether, the title compound is obtained in a yield of 0.85 g (0.00228 mole, 77%), m.p.: 104°–107° C.

¹H-NMR (CDCl₃, δppm): 2.1

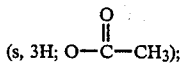

2.55 (s, 3H; N—CH₃), 2.71

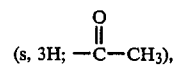

4.05 (s, 2H; —CH₂OH), 6.41 (s, 1H; olefinic), 7.11 (m, 3H; arom).

IR (KBr), cm⁻¹: 2780 (aliphatic next to N); 1730 (ester carbonyl); 1690 (acid amide carbonyl); 1263 (ester C—O—C); 1600–1575 (arom nucleus); 780 arom. deform.).

EXAMPLE 20

Preparation of 1-acetyl-8-acetyloxymethyl-2-chloro-6-methyl-8-ergolene 1.0 g of 1-acetyl-8-acetyloxymethyl-6-methyl-8-ergolene is chlorinated and the product is isolated by using the process of Example 19. The title compound is obtained in a yield of 0.78 g (0.0021 mole, 71%), m.p.: 105°–107° C.

¹H-NMR (CDCl₃, δppm): 2.05

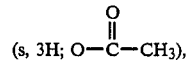

2.45 (s, 3H; N—CH₃), 2.71

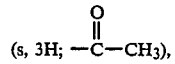

4.55 (s, 2H; —CH₂—O), 7.21 (m, 3H; arom.).

IR (KBr), cm⁻¹: 2780 (aliphatic next to N); 1726 (ester carbonyl); 1690 (acid amide carbonyl); 1257 (ester C—O—C); 1598–1573 (arom. nucleus); 780 (arom. deform.).

EXAMPLE 21

Preparation of 1-acetyl-8-acetyloxymethyl-2-bromo-6-methyl-9-ergolene 1.0 g of 1-acetyl-8-acetyloxymethyl-6-methyl-9-ergolene is halogenated by using the process of Example 19, except that 3.2 ml of trimethylbromosilane are employed instead of trimethylchlorosilane. The title compound is obtained in a yield of 0.9 g (0.0021 mole, 73%).

¹H-NMr (CDCl₃, δ ppm): 2.15

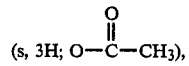

2.6 (s, 3H; N—CH₃), 2.8

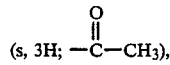

4.1 (s, 2H; —CH₂—), 6.51 (s, 1H; olefinic); 7.2(m, 3H; arom.).

IR (KBr), cm⁻¹: 2780 (aliphatic next to N); 1730 (ester carbonyl); 1690 (acid amide carbonyl); 1260 (ester C—O—C); 1600–1570 (arom. nucleus).

EXAMPLE 22

Preparation of 8-chloromethyl-6-methyl-9-ergolene 1.7 ml of phosphorus oxychloride are added to a solution of 1 g of lysergol in 20 ml of dimethylformamide. The mixture is heated at 80° C. for 10 minutes, then cooled down and poured into a 5-fold volume of ice-water. The pH value of the solution is adjusted to 8 by adding aqueous ammonia, the precipitate is filtered off and dried to give the title compound in a yield of 0.9 g (0.0033 mole, 84%), m.p.: 206°–207° C.

[α]_D^{20} = +86.9° (c=0.46, pyridine).

EXAMPLE 23

Preparation of 8-chloromethyl-1-formyl-6-methyl-9-ergolene 3.4 ml (7 equivalents) of phosphorus oxychloride are added to a solution of 2.0 g of 8-chloromethyl-6-methyl-9-ergolene in 30 ml of anhydrous dimethylformamide, then the solution is stirred at 60° C. for 5 hours. After completion of the reaction, the mixture is cooled down, poured into 250 ml of ice-water and made alkaline by adding aqueous ammonia up to a pH value of 7.5. The mixture is extracted 3 times with 20 ml of chloroform each, the combined organic phase is washed with 20 ml of water, dried over anhydrous sodium sulfate, filtered off and evaporated under reduced pressure. The oily residue is dissolved in 10 ml of dichloromethane and sed through a column prepared from 10 g of Kieselgel. The eluate is evaporated under reduced pressure to give the title compound in a yield of 1.4 g (0.00466 mole, 63%).

$^1$H-NMR (CDCl$_3$, δ ppm): 2.64 (s, 3H; N—CH$_3$), 3.65 (m, 2H; CH$_2$—), 6.54 (s, 1H; olefinic), 7.2–8.4 (m, 4H; arom.), 9.52 (s, 1H; formyl).

IR (KBr), cm$^{-1}$: 1680 (acid amide carbonyl); 1600–1575 (arom. nucleus).

EXAMPLE 24

Preparation of 2-chloro-8-chloromethyl-1-formyl-6-methyl-9-ergolene

Following the process of Example 19,1 g of 8-chloromethyl-1-formyl-6-methyl-9-ergolene are reacted with 2.5 ml of trimethylchlorosilane and the product is isolated to give the title compound in a yield of 0.8 g (0.0024 mole, 72%), m.p.: 159°–160° C.

$^1$H-NMR (CDCl$_3$, δ ppm): 2.64 (s, 3H; N—CH$_3$), 3.65 (m, 2H; CH$_2$), 6.47 (s, 1H; olefinic), 7.2–8.4 (m, 3H; arom.), 9.52 (s, 1H; formyl).

IR (KBr), cm$^{-1}$: 1680 (acid amide carbonyl); 1600–1575 (arom. nucleus).

EXAMPLE 25

Preparation of 2-chloro-1-methyllumilysergol (2-chloro-1,6-dimethyl-8-hydroxymethyl-10-methoxyergoline)

2.5 ml of trimethylchlorosilane are portionwise added to 20 ml of dimethylsulfoxide under stirring and after stirring for 15 minutes, a solution of 1 g of 1-methyllumilysergol (1,6-dimethyl-8-hydroxymethyl-10-methoxyergoline) in 5 ml of dimethylsulfoxide is added. The mixture is stirred at room temperature for 25 minutes, then poured into 140 ml of water. The pH value is adjusted to 8 to 9 by adding aqueous ammonia and the mixture is extracted 3 times with 30 ml of dichloromethane each. The organic phase is dried over anhydrous sodium sulfate, filtered and evaporated under reduced pressure. After recrystallization of the residue from acetone, the title compound is obtained in a yield of 0.87 g (0.0026 mole, 78%), m.p.: 252° C.

$^1$H-NMR (DMSO-d$_6$+TFA, δ ppm): 2.50 (s, 3H; N—CH$_3$), 2.85 (s, 3H; —OCH$_3$), 3.55 (m, 2H; —CH$_2$OH), 3.73 (s, 3H; indole N—CH$_3$), 7.13–7.44 (m, 3H; arom.).

IR (KBr), cm$^{-1}$: 2910 (OCH$_3$); 2820 (indole CH$_3$); 780 (arom. halogen).

EXAMPLE 26

Preparation of 2-chloronicergoline (8-[(5-bromonicotinoyl)oxymethyl]-2-chloro-1,6-dimethyl-10-methoxyergoline)

Following the process of Example 25, 1 g of nicergoline (8-[(5-bromonicotinoyl)oxymethyl]-1,6-dimethyl-10-methoxyergoline) is reacted with 1.6 ml of trimethylchlorosilane and the obtained product is isolated by chromatography on a Kieselgel column, using a 7:3 mixture of benzene and acetone as eluant, to give the title compound in a yield of 0.65 g (0.00125 mole, 60%).

$^1$H-NMR (CDCl$_3$, δ ppm): 2.48 (s, 3H; N—CH$_3$), 2.53 (s, 3H; O—CH$_3$), 3.74 (s, 3H; indole N—CH$_3$), 7.0–7.28 (m, 3H; arom. hydrogens, indole), 8.45 (t, 1H; arom. H), 8.9 (d. 1H; arom. H), 9.2 (d, 1H; arom. H).

EXAMPLE 27

Preparation of 2-bromo-agroclavine (2-bromo-6,8-dimethyl-8-ergolene)

Following the process of Example 25, 1 g of agroclavine (6,8-dimethyl-8-ergolene) is reacted with 3.2 ml of trimethylbromosilane and the product is isolated as described in Example 25 give the title compound in a yield of 1.1 g (0.00347, 82.6%), m.p.: 195° C.

EXAMPLE 28

Preparation of 2-bromolysergic acid methyl ester

Following the process of Example 25, 1 g of lysergic acid methyl ester is reacted with 2.7 ml of trimethylbromosilane and the product is purified by chromatography on a Kieselgel column by using a 7:3 mixture of benzene and acetone as eluant. After recrystallization from benzene, the title compound is obtained in a yield of 0.7 g (0.0019 mole, 55%), m.p.: 177°–178° C., $[α]_D^{20}= +41°$ (c=1, chloroform).

EXAMPLE 29

Preparation of 2-bromolysergic acid 20 ml of 20% aqueous potassium hydroxide solution are added to the solution of 1 g of 2-bromolysergic acid methyl ester in 6 ml of ethanol, then the solution is stirred in a bath of 80° C. for one hour. The pH value of the solution cooled down is adjusted to 7 by adding aqueous hydrochloric acid. The crystalline precipitate obtained on cooling is filtered off, washed with water and dried to give the title compound in a yield of 0.5 g (0.0014 mole, 50%).

EXAMPLE 30

Preparation of 2-bromo-α-ergocryptine 1.3 ml of trimethylbromosilane (6 equivalents as calculated for α-ergocryptine to be brominated) are added to 40 ml of anhydrous dimethylsulfoxide and the solution is stirred at room temperature for 15 minutes. After adding 1 g (0.001739 mole) of α-ergocryptine, the mixture is stirred at room temperature for 10 minutes, then poured into 200 ml of ice-water and the pH value is adjusted to 8–9 by adding aqueous ammonia. The aqueous solution is extracted 3 times with 50 ml of dichloromethane each, then the combined organic phase is washed 3 times with 30 ml of 10% sodium chloride solution each. The dichloromethane solution is dried over anhydrous sodium sulfate, filtered and evaporated to 10 ml under reduced pressure. The residue is led through an aluminum oxide column moistened with 10 g of an 1:1 mixture of dichloromethane and ethyl acetate. The first fraction of 50 ml volume (containing the 2-bromo-α-ergocryptine) is evaporated to dryness, the residue is dissolved in 10 ml of dichloromethane, then 30 ml of diisopropyl ether are added to the residue and concentrated to its half volume under environmental pressure. The white crystalline precipitate is filtered off, washed and dried to give the title compound in a yield of 1.06 g (0.001617 mole, 93%), m.p.: 218° C., $[α]_D^{20}= -195°$ (c=1, dichloromethane).

EXAMPLE 31

Preparation of 2-bromo-α-ergocryptine methanesulfonate 30 ml of methyl ethyl ketone are added to a solution of 1.06 g (0.001617 mole) of 2-bromo-α-ergocryptine base in 20 ml of dichloromethane. After adding the calculated amount (molar equivalent) of methanesulfonic acid (0.152 g), a crystalline precipitate is separated which is washed with 5 ml of methyl ethyl ketone and dried to give the title methanesulfonate salt in a yield of 1.1 g (0.001466 mole, 90.6%), m.p.: 192°–196° C., $[\alpha]_D^{20} = +95°$ (c=1, dichloromethane-methanol (1:1)).

EXAMPLE 32

Preparation of 2-bromo-α-ergocryptine

Following the process of Example 30, 1 g of α-ergocryptine phosphate is brominated with 2.0 ml of trimethylbromosilane. After isolating, the title base is obtained in a yield of 0.9 g (0.001359 mole, 91.5%), m.p.: 218° C., $[\alpha]_D^{20} = -195°$ (c=1, dichloromethane).

EXAMPLE 33

Preparation of 2-bromo-α-ergocryptine 9.1 ml of trimethylbromosilane are added to 1000 ml of anhydrous dimethylsulfoxide and the solution is stirred at room temperature for 15 minutes, then 10 g of a base mixture of α-ergocryptine and ergosine are added, which contains 64.2% of α-ergocryptine base, 28.46% of ergosine base, 2.78% of α-ergocryptinine base and 1.96% of ergosinine base. After stirring for 20 minutes, the mixture is poured into 5 liters of ice-water and the pH is made alkaline up to a value of 8 to 9 by adding aqueous ammonia. The mixture is extracted 3 times with 500 ml of dichloromethane each, the organic phases are combined and washed 3 times with 200 ml of 10% sodium chloride solution each. The dichloromethane phase is dried over anhydrous sodium sulfate, filtered and evaporated under reduced pressure. The residue is purified on a Kieselgel column by using ethyl acetate as eluant to give the title compound in a yield of 6.3 g (0.00967 mole, 87%) (as calculated for the starting base mixture), m.p.: 218° C.; as well as 2.9 g (0.0046 mole, 89%) of 2-bromoergosine, m.p.: 183°–185° C.

EXAMPLE 34

Preparation of 2-bromo-α-ergocryptine

Following the process of Example 33, 10 g of a mixture of α-ergocryptine phosphate and ergosine phosphate (containing 48.9% of α-ergocryptine base, 1.9% of α-ergocryptinine base, 28.2% of ergosine base and 1.3% of ergosinine base) is brominated with 20 ml of trimethylbromosilane and the title compound is isolated in a yield of 4.7 g (0.007243 mole, 85%), m.p.: 218° C. $[\alpha]_D^{20} = -195°$ (c=1, dichloromethane).

EXAMPLE 35

Preparation of 2-bromo-α-ergocryptinine

Following the process of Example 30, 1 g of α-ergocryptinine base is brominated with 1.4 ml of trimethylbromosilane. The title compound is isolated in a yield of 1.0 g (0.00151 mole, 87%), m.p.: 173°–184° C., $[\alpha]_D^{20} = +143°$ (c=1, chloroform).

EXAMPLE 36

Preparation of 2-bromo-α-ergocryptinine oxalate

A solution of 0.14 g (1.01 equivalents) of oxalic acid in 4 ml of ethanol is added to a solution of 1 g of 2-bromo-α-ergocryptinine in 10 ml of ethanol under stirring. The crystalline precipitate is filtered, washed and dried to give the title oxalate in a yield of 0.9 g (89%), m.p.: 183°–185° C., (c=1, pyridine).

EXAMPLE 37

Preparation of 2-bromoergosine

Following the process of Example 30, 1 g of ergosine is brominated with 1.4 ml of trimethylbromosilane. The title compound is isolated in a yield of 1.1 g (0.001716 mole, 94%), m.p.: 183°–185° C., $[\alpha]_D^{20} = -91.6°$ (c=1, methanol).

EXAMPLE 38

Preparation of 2-bromoergotamine

Following the process of Example 30, 1 g of ergotamine is brominated with 1.4 ml of trimethylbromosilane. The title compound is isolated in a yield of 1.03 g (0.001564 mole, 91%), m.p.: 195°–197° C., $[\alpha]_D^{20} = -163°$ (c=1, chloroform).

EXAMPLE 39

Preparation of 2-bromoergocristine

Following the process of Example 30, 1 g of ergocristine is brominated with 1.4 ml of trimethylbromosilane. The title compound is isolated in a yield of 1.0 g (0.00146 mole, 89%), $[\alpha]_D^{20} = -189°$ (c=1, chloroform).

EXAMPLE 40

Preparation of 2-bromoergocornine

Following the process of Example 30, 1 g of ergocornine is brominated with 1.4 ml of trimethylbromosilane. The title compound is isolated in a yield of 1.0 g (0.001548 mole, 87%), m.p.: 187°–193° C., $[\alpha]_D^{20} = -215°$ (c=1, chloroform).

EXAMPLE 41

Epimerization of 2-bromo-α-ergocryptinine

To the solution of 2 g of 2-bromo-α-ergocryptinine in 9.0 ml of acetone and 1.0 ml of methanol, 0.4 ml of glacial acetic acid and 0.2 ml of concentrated phosphoric acid are added at room temperature under stirring. After stirring at 55° C. for 3 hours and after standing at room temperature overnight, the crystalline precipitate is filtered, washed 3 times with 10 ml of acetone each and dried to give 2-bromo-α-ergocryptine phosphate in a yield of 1.94 g (0.00258 mole, 74%), m.p.: 191°–194° C.

Isolation of a second crop (second generation) of 2-bromo-α-ergocryptine phosphate is carried out as follows:

The mother liquor and the acetone washings are combined and evaporated under reduced pressure. The residue is dissolved in 15 ml of 5% tartaric acid solution, clarified with 0.5 g of activated charcoal, filtered off and the charcoal is washed twice with 4 ml of 5% tartaric acid solution each. The pH of the filtrate is adjusted to a value of 8 to 9 by adding aqueous ammonia, the precipitated base is filtered, washed 3 times with 10 ml of water each and dried. The epimerization is carried out as described in Example 41 to give 0.3 g (0.0004 mole, 11.5%) of 2-bromo-α-ergocryptine phosphate.

EXAMPLE 42

Preparation of 2-bromo-dihydroergotamine

Following the process of Example 30, 1 g of dihydroergotamine base is reacted with trimethylbromosilane. The obtained product is recrystallized from acetone to give the title compound in a yield of 0.95 g (0.00143 mole, 83.6%), m.p.: 189°–199° C.

We claim:

1. A process for the preparation of a compound of the Formula (I)

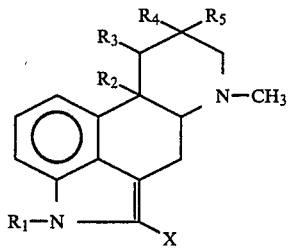

wherein

X is halogen;

$R_1$ is hydrogen, $C_1$ to $C_4$ alkyl, $C_1$ to $C_6$ alkanoyl, benzoyl, naphthoyl, phenylacetyl, 3-phenylpropionyl, picolyl, furoyl, nicotinoyl, isonicotinoyl, trimethoxybenzoyl, 4-chlorobenzoyl, 2-chlorobenzoyl, 5-bromonicotinoyl, or pyroglutamyl;

$R_2$, $R_3$, and $R_4$ are each hydrogen, or $R_2$ together with $R_3$, or $R_3$ together with $R_4$, respectively, form an additional chemical bond; and $R_5$ is hydroxymethyl, methoxycarbonyl, carboxyl, —$CH_2OR$, wherein R is $C_1$ to $C_6$ alkanoyl, benzoyl, naphthoyl, phenylacetyl, 3-phenylpropionyl, picolyl, furoyl, nicotinoyl, isonicotinoyl, trimethoxybenzoyl, 4-chlorobenzoyl, 2-chlorobenzoyl, 5-bromonicotinoyl, or pyroglutamyl; or $R_5$ is —$CH_2X$, wherein X is halogen; or $R_5$ is a —CO—NH—(a) group

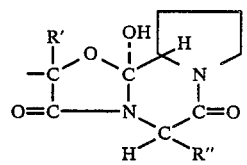

wherein

R' is methyl or isopropyl; and

R" is benzyl, isopropyl, or isobutyl; or $R_1$ is methyl;

$R_2$ is methoxy;

$R_3$ and $R_4$ are each hydrogen; and $R_5$ is hydroxymethyl or a —$CH_2OR$ group, wherein R is 5-bromonicotinoyl; or $R_1$ and $R_2$ stand for hydrogen;

$R_3$ and $R_4$ stand for an additional chemical bond; and $R_5$ is methyl;

or a pharmaceutically acceptable acid addition salt thereof, which comprises the step of selectively halogenating a compound of the Formula (II)

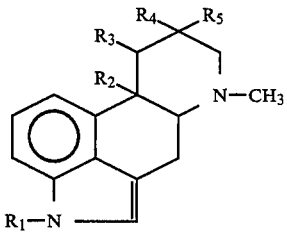

wherein $R_1$, $R_2$, $R_3$, $R_4$, and $R_5$ are as defined above or a pharmaceutically acceptable acid addition salt thereof, by employing a halogenating agent consisting essentially of dimethylsulfoxide and a trialkylhalosilane or a triphenylhalosilane.

2. A process as claimed in claim 1, which comprises using trimethylchlorosilane, trimethylbromosilane or trimethyliodosilane as a trialkylhalosilane compound.

3. A process as claimed in claim 1, which comprises using a triphenylchlorosilane, triphenylbromosilane or triphenyliodosilane as a triarylhalosilane compound.

4. A process for the preparation of 2-bromo-α-ergocryptine or a pharmaceutically acceptable acid addition salt thereof by the bromination of α-ergocryptine or a pharmaceutically acceptable acid addition salt thereof or by the bromination of a crude base mixture containing other ergot alkaloids in addition to α-ergocryptine or pharmaceutically acceptable acid addition salts thereof, which comprises carrying out the bromination by using a system consisting of dimethylsulfoxide, a trialkylbromosilane or a triphenylbromosilane and optionally hydrogen bromide at room temperature and, if desired, separating the thus-obtained 2-bromo-α-ergocryptine or converting same into a pharmaceutically acceptable acid addition salt.

* * * * *